United States Patent [19]

Hollowood

[11] Patent Number: 4,584,407
[45] Date of Patent: Apr. 22, 1986

[54] PREPARATION OF THIAZOLIDINE DERIVATIVES

[75] Inventor: John Hollowood, York, England

[73] Assignee: Fine Organics Limited, Middlesbrough, England

[21] Appl. No.: 330,015

[22] Filed: Dec. 11, 1981

[51] Int. Cl.$^4$ .......................................... C07D 277/04
[52] U.S. Cl. ...................................... 564/487; 548/146
[58] Field of Search ................ 548/146; 564/341, 413, 564/487, 801, 500

[56] References Cited

U.S. PATENT DOCUMENTS 4,011,233  3/1977  Dobs .................................. 548/146

FOREIGN PATENT DOCUMENTS 2922785  12/1979  Fed. Rep. of Germany ....... 564/500
4720111   9/1972  Japan ................................. 564/487

OTHER PUBLICATIONS

Sandler et al, Org. Functional Group Prep. pp. 480–481 (1968).

*Primary Examiner*—Robert Gerstl
*Attorney, Agent, or Firm*—Bert J. Lewen; Henry Sternberg

[57] ABSTRACT

A method of preparing a thiazolidine derivative of the formula

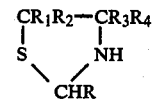

where R, $R_1$, $R_2$, $R_3$ and $R_4$ are each independently hydrogen or appropriate aromatic or aliphatic substituents, comprises reacting together a sulphur donor, such as sulphur or hydrogen sulphide, an aldehyde of the formula RCHO, such as benzaldehyde or formaldehyde, and an ethanolamine derivative of the formula, or including the radical, $NH_2CR_1R_2CR_3R_4X$, where X is a leaving group. A suitable derivative may be, for instance, aminoethylsulphate (AES). The thiazolidine derivative may be used, for example, as intermediates in the preparation of other compounds such as cysteamine.

5 Claims, No Drawings

PREPARATION OF THIAZOLIDINE DERIVATIVES

This invention relates to methods for preparing thiazolidine derivatives which are useful, inter alia, as intermediates for the preparation of other compounds, for instance, cysteamine or derivatives thereof.

Known methods for the preparation of cysteamine are expensive, time consuming, require special equipment and/or involve the use of materials which are sometimes difficult to acquire and/or may be difficult to handle. A known method for the preparation of cysteamine involves the treatment of aminoethyl hydrogen sulphate (AES) with carbon disulphide. The product of this reaction is 2-mercapto thiazoline. This product may be hydrolysed with dilute acid, e.g. hydrochloric acid to form cysteamine hydrochloride with the evolution of carbon dioxide and hydrogen sulphide. A high yield is obtained but the hydrolysis reaction is slow, typically taking fourteen days to complete, and there are problems associated with the handling of the by-product hydrogen sulphide.

In a second known process hydrogen sulphide is reacted with ethyleneimine which produces directly cysteamine. However, ethyleneimine is a toxic substance being carcinogenic and again there are the difficulties in handling hydrogen sulphide, in this case as one of the reactants of the process.

In a third known process a 2-H-2-oxazoline or a 2-alkyl-2-oxazoline is reacted with hydrogen sulphide to form the corresponding N-(2-mercaptoethyl)alkanamide which may then be hydrolysed under acid conditions to form the acid salt of cysteamine. This process requires use of hydrogen sulphide under pressure, thereby involving expensive high pressure equipment as well as the difficulties with regard to the availability of hydrogen sulphide and the handling of this gas.

According to the present invention there is provided a method for the preparation of a thiazolidine derivative of the formula

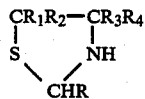

where R, $R_1$, $R_2$, $R_3$ and $R_4$ are each independently hydrogen or appropriate aromatic or aliphatic substituents, the method comprising reacting together a sulphur donor, an aldehyde of the formula RCHO where R is as defined above, and an ethanolamine derivative of the formula or including the radical $XCR_1R_2CR_3R_4NH_2$ where $R_1$, $R_2$, $R_3$ and $R_4$ are as defined above and X is a leaving group.

Where the ethanolamine derivative is a compound of the formula $XCR_1R_2CR_3R_4NH_2$, it may be, for instance, a hydrogen sulphate such as aminoethylsulphate (AES) or another acid salt.

Where the ethanolamine derivative includes a radical of the formula $XCR_1R_2CR_3R_4NH_2$ it is preferably a compound of the formula $XCR_1R_2CR_3R_43Y^-NH_3$ where Y is the anion of an acid such as hydrochloric or hydrobromic acid.

Examples are:

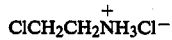

Preferably the substituents $R_1$, $R_2$, $R_3$ and $R_4$ are hydrogen or lower alkyl (preferably $C_1-C_6$ alkyl, more preferably $C_1-C_3$ alkyl).

The sulphur donor may be any suitable source of sulphur, for instance, sulphur itself, a sulphide, a hydrosulphide or hydrogen sulphide. Preferably the sulphur donor is an ammonium or alkali metal sulphide or hydrosulphide, for instance, the alkali metal sulphide sodium sulphide. Preferably the sulphur donor is the last reactant to be added, the aldehyde being present in the reaction mixture to ensure that cysteamine formed during the reaction is converted to the thiazolidine.

The aldehyde may be an aliphatic or aromatic aldehyde. A preferred aromatic aldehyde is benzaldehyde. Aliphatic aldehydes include formaldehyde and aldehydes in which R is alkyl, preferably lower alkyl.

A preferred reaction is that between a sulphur donor, preferably sodium sulphide, aminoethylsulphate and benzaldehyde to form 2-phenylthiazolidine. Preferably the reaction mixture is heated to a temperature of at least 50° C., more preferably to reflux, after addition of the sulphur donor to the other reactants. Preferably, the sulphur donor is used in excess, more preferably about 10% excess.

The thiazolidine derivative prepared by the method of the present invention is a useful intermediate for the preparation of other compounds. For instance, the thiazolidine derivative may be hydrolysed to form cysteamine (or a derivative thereof) or an acid salt thereof. The hydrolysis may be carried out under acid conditions, typically dilute or concentrated acid conditions using an inorganic acid such as hydrochloric acid or an organic acid such as acetic or oxalic acid. Such hydrolysis is comparatively fast taking perhaps half an hour for completion.

In the case where $R_1$, $R_2$, $R_3$ and $R_4$ are all hydrogen, the product is the acid salt of cysteamine. Where the aldehyde is benzaldehyde, then this material is released on hydrolysis and may be recovered as a distillate as a result of the hydrolysis reaction. Benzaldehyde is relatively easy to handle and may be recycled for use in the formation of the thiazolidine derivative. If hydrochloric acid is used only a slight excess of acid to thiazolidine is preferably used, otherwise there is formation of the dithio acetal having the formula

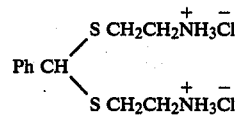

If an organic acid is used and the hydrochloride of cysteamine is required then hydrochloric acid should be added at the end of the reaction. In the case of acetic acid the acetic acid formed is then distilled out with the water to give the hydrochloride. However, with oxalic acid the liquors should be cooled to 0°-5° C. and the oxalic acid formed should be filtered off before distilling to dryness to give the required hydrochloride.

Cysteamine may be used, for instance, as an intermediate for the production of anti-ulcer drugs.

The thiazolidine derivative formed by a method in accordance with the present invention may be reacted with compounds having one or more active hydrogens to replace the, or one or more, active hydrogens with a group of the formula $-S-CR_1R_2CR_3R_4NH_2$. The reaction is carried out in the presence of dilute acid, either mineral or organic acid. For example, the thiazolidine derivative may be reacted with an alcohol of the formula R'OH to form a compound of the formula:

$$R'-S-CR_1R_2CR_3R_4NH_2$$

or an acid salt thereof.

An embodiment of the present invention will now be described by way of example only.

PREPARATION OF 2-PHENYLTHIAZOLIDINE

Benzaldehyde (530 g.), aminoethylsulphate (705 g.) and water (840 g.) are stirred together. Sodium sulphide flake (62%) (692 g., 10% molar excess) is added over ca. two hours allowing the reaction mixture to exotherm to 40°–50° C. When the sulphide addition is complete the reaction mixture is heated to reflux and held at reflux for six hours before cooling to 60° C. Water (1100 ml.) is added (to hold the sodium sulphate in solution), and the reaction is cooled to 20°–25° C. The precipitated product is filtered, washed with water (3×200 ml.) and dried at 60° C. under vacuum to give 742 g. 2-phenyl-thiazolidine (90% based on aminoethylsulphate).

Equimolar ratios of benzaldehyde and aminoethylsulphate give the optimum yield but an excess of benzaldehyde does not affect the reaction.

Aminoethylsulphate in the above reaction can be replaced by 2-aminoethylchloride hydrochloride (580 g.). The yield obtained is 725 g. (88%).

The reaction can be run under much more dilute conditions, but this results in a drop in yield, e.g. doubling the quantity of water used in the above example would lower the yield to 75%.

The reaction will proceed at temperatures other than reflux but is very slow below 50° C. In the above example a reaction temperature of 70° C. reduced the yield obtained after six hours to 70%.

HYDROLYSIS OF 2-PHENYLTHIAZOLIDINE USING ACETIC ACID

Water (240 ml.), 2-phenylthiazolidine (99 g.) and glacial acetic acid (42 g.) are mixed and heated to reflux. The benzaldehyde formed is azeotroped out using a Dean Stark head. When the reaction is complete, hydrochloric acid (70 ml.) is added and the reaction liquors distilled to dryness under vacuum. Isobutanol (110 g.) is added and the liquors cooled to 5°–10° C. The precipitated product is filtered off and dried under vacuum at 60° C. to give 61 g. cysteamine hydrochloride (90% yield).

HYDROLYSIS OF 2-PHENYLTHIAZOLIDINE USING HYDROCHLORIC ACID

Water (240 ml.), 2-phenylthiazolidine (99 g.) and concentrated hydrochloric acid (73 g.) are heated to reflux. The benzaldehyde formed is azeotroped out using a Dean Stark head. When the reaction is complete the liquors are distilled to dryness under vacuum and the crystalline mass remaining is recrystallised from isopropanol (100 ml.) to give 58 g. cysteamine hydrochloride (85% yield).

I claim:

1. A method for the preparation of a thiazolidine derivative of the formula

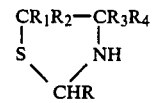

where R is phenyl and $R_1$, $R_2$, $R_3$ and $R_4$ are each independently hydrogen or $C_1-C_6$ alkyl, comprising reacting together at atmospheric pressure a sulfur donor, said donor selected from the group consisting of an alkali metal sulfide and an alkali metal hydrosulfide, benzaldehyde and an ethanolamine derivative of the formula, or including the radical, $XCR_1R_2CR_3R_4NH_2$ where $R_1$, $R_2$, $R_3$ and $R_4$ are as defined above and X is a leaving group.

2. A method in accordance with claim 1 wherein said sulfur donor is added to a mixture of said aldehyde and said ethanolamine derivative.

3. A process in accordance with claim 1 wherein $R_1$, $R_2$, $R_3$ and $R_4$ are each hydrogen.

4. A method for the preparation of cysteamine or an acid salt thereof comprising reacting together at atmospheric pressure a sulfur donor, said donor selected from the group consisting of an alkali metal sulfide and an alkali metal hydrosulfide, with benzaldehyde and an ethanolamine derivative of the formula, or including the radical, $XCH_2CH_2NH_2$ where X is a leaving group whereby a thiazolidine derivative of the formula

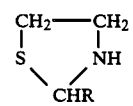

where R is phenyl, is formed, thereafter hydrolyzing said thiazolidine derivative under acid conditions.

5. A method in accordance with claim 4 wherein said hydrolysis is effected by means of an acid selected from the group consisting of hydrochloric acid and acetic acid.

* * * * *

UNITED STATES PATENT AND TRADEMARK OFFICE
CERTIFICATE OF CORRECTION

PATENT NO. : 4,584,407

DATED : April 22, 1986

INVENTOR(S) : JOHN HOLLOWOOD

It is certified that error appears in the above-identified patent and that said Letters Patent is hereby corrected as shown below:

On the cover of the patent, left column, insert after the application filing date, the following:

[30] --Foreign Application Priority Data
December 12, 1980  [GB]  United Kingdom   8039922

Signed and Sealed this

Twelfth Day of August 1986

[SEAL]

Attest:

DONALD J. QUIGG

Attesting Officer

Commissioner of Patents and Trademarks